US005600039A

United States Patent [19]

Galland et al.

[11] Patent Number: 5,600,039
[45] Date of Patent: Feb. 4, 1997

[54] PROCESS FOR THE PREPARATION OF 1,1,1,2-TETRAFLUOROETHANE

[75] Inventors: Jean-Michel Galland, Vernaison; Emmanuel Guiraud, Saint-Genis Laval; Jean-Pierre Schirmann, Paris, all of France

[73] Assignee: d'Elf Atochem S.A., France

[21] Appl. No.: 363,553

[22] Filed: Dec. 23, 1994

Related U.S. Application Data

[63] Continuation of Ser. No. 279,622, Jul. 25, 1994, abandoned, which is a continuation of Ser. No. 10,043, Jan. 28, 1993, abandoned.

[30] Foreign Application Priority Data

Jan. 30, 1992 [FR] France .................. 92 01035

[51] Int. Cl.⁶ .................................................. C07C 17/08
[52] U.S. Cl. .................................. 570/169; 570/168
[58] Field of Search ................................ 570/169, 168

[56] References Cited

U.S. PATENT DOCUMENTS 4,158,675  6/1979  Potter ........................ 570/169

FOREIGN PATENT DOCUMENTS

0449617A2  10/1991  European Pat. Off. .
2030981    4/1980   United Kingdom .
WO90/08755 8/1990   WIPO .

*Primary Examiner*—Alan Siegel
*Attorney, Agent, or Firm*—Spencer & Frank

[57] ABSTRACT

The subject of the invention is a continuous process for the preparation of 1,1,1,2-tetrafluoroethane (134a) from 2-chloro-1,1,1-trifluoroethane (133a) and hydrofluoric acid in the gaseous phase in the presence of a chromium-based catalysts.

According to the invention, the flow of gas leaving the reactor is subjected to a distillation in order to separate at the top a flow containing almost all the HCl and at least 90% of the 134a produced by the reaction and at the bottom a flow containing at least 90% of the unconverted reactants (133a and HF), and the latter flow is recycled directly to the reactor, without any purifying operation.

20 Claims, 1 Drawing Sheet

PROCESS FOR THE PREPARATION OF 1,1,1,2-TETRAFLUOROETHANE

This is a continuation of application Ser. No. 08/279,622, filed on Jul. 25, 1994 now abandoned which is a continuation of co-pending application Ser. No. 08/010,043, filed on Jan. 28, 1993 now abandoned.

FILED OF THE INVENTION

The present invention relates to a continuous process for the preparation of 1,1,1,2-tetrafluoroethane from 2-chloro-1,1,1-trifluoroethane and hydrofluoric acid HF.

BACKGROUND OF THE INVENTION 1,1,1 2-tetrafluoroethane, technically known by the designation 134a, is mainly intended to replace dichlorodifluoromethane (CFC 12) in its applications to refrigeration.

Its preparation by fluorination in the gaseous phase of 2-chloro-1,1,1-trifluoroethane (technically known by the designation 133a) has already been the subject of numerous patents.

U.S. Pat. No. 4,158,675 describes a process for the preparation of 134a by reacting in the vapor phase at a high temperature a haloethane of formula $CX_3CH_2Cl$ where X represents Br, Cl or F, with HF in the presence of a chromic oxide based catalyst; the 134a produced, containing 2-chloro-1,1-difluoroethylene as an impurity, is then brought into contact with HF on the same chromic oxide based catalyst, at a temperature between 100° and 275° C. so as to reduce the haloethylene content. The example provided in this patent (trial duration: 3 hours) gives no information on possible recycling of the unconverted 133a and HF reactants.

Patent Application JP 55 27138/80 describes a process for the preparation of 134a by reacting 133a with HF in a molar proportion of 1 in 3 to 20 in the presence of an inorganic chromium (III) compound at a temperature of 300° to 450° C. The examples give no information on possible recycling of the unconverted reactants and the duration of the trials.

Patent FR 2,433,500 describes a process for the preparation of 134a by reacting 133a with HF in the presence of a chromium (III) inorganic compound, characterized in that from 0.002 to 0.05 mol of oxygen per mol of 133a is introduced into the reaction system. The examples give no information on possible recycling of the unconverted reactants. The results obtained during certain trials conducted in the presence of oxygen show stable reaction performances over 85 hours.

Patent Application EP 328,127 recommends, as a catalyst, the use in the presence of oxygen of metals other than chromium, namely Co, Mn, Ni, Pd, Ag and/or Ru on $AlF_3$, so as to minimize oxidation into chlorine and water of the hydrochloric acid formed leading to a loss in selectivity and a corrosion risk. The examples provided in this patent application give no information on possible recycling of the unconverted reactants. The results obtained during certain trials (carried out with oxygen, on catalysts containing no chromium) show stable reaction performances over 9 hours (Example 1) and 19 hours (Example 2).

The subject of Patent Application EP 331,991 is a process for the preparation of 134a consisting in bringing into contact, in the gaseous phase between 300° and 500° C., 133a and HF on a catalyst containing at least one metal which has an oxidation number greater than zero and is selected from the metals in groups VIII, VII B, III B, I B and/or metals having an atomic number of 58 to 71, then in separating 134a from the leaving flow of gas. The examples illustrating this process give no information on possible recycling of the unconverted reactants. A fall in activity appears after 38 hours (Example 1) or 21 hours (Example 2).

In Patent Application JP 262,946/89 it is indicated that the known methods for maintaining the activity of a fluorination catalyst, such as continuous addition of chlorine or oxygen are not suitable in the case of the fluorination of a halogenated hydrocarbon containing hydrogen (such as 133a) by virtue of the loss of selectivity observed. This publication therefore proposes a process of periodic regeneration of the oxygen catalyst consisting in that, when the activity of the catalyst decreases during the reaction, introduction of the reactants is stopped and a gas containing oxygen is fed to the reaction system in order to reactivate the catalyst, then this feeding with gas containing oxygen is stopped and feeding with reactants is resumed. Examples 2 and 4, and comparative Examples 1 and 2 relate to fluorination of 133a, using catalysts containing chromium, in the presence or absence of oxygen. A fall in activity of these catalysts is noticed. The examples provided in this publication give no information on possible recycling of the unconverted reactants.

In Patent Application JP 172,933/90 whose subject is a process for fluorination of 133a, it is indicated that traditional catalysts, such as chromic oxide on its own, have a low activity at low temperatures and a short lifetime at high temperatures. It therefore proposes carrying out the reaction between 133a and HF in the presence of a fluorination catalyst based on halides or oxides of chromium and on at least one element selected from Al, Mg, Ca, Ba, Sr, Fe, Ni, Co and Mn. It also recommends, together with the specified catalyst, feeding of oxygen or chlorine on the basis of 0.1 to 10 mol % with respect to 133a. All the examples provided use 2 mol % oxygen and are conducted without recycling the unconverted reactants.

Patent Application WO 90/08,755 describes an improved process for the preparation of 134a from trichloroethylene, the improvement consisting in conducting the catalytic fluorination reaction in a single reaction zone fed with trichloroethylene, with HF and recycled 133a, the reaction being able to be carried out in the presence or absence of oxygen. The examples provided are conducted without recycling the unconverted reactants.

Patent Application EP 408,005 describes a process for the preparation of 134a by reacting in the gaseous phase trichloroethylene and hydrofluoric acid in the presence of 133a, the mole ratio of trichloroethylene to 133a ranging from 5/95 to 50/50, and in the presence of a catalyst comprising chromium trioxide supported on $AlF_3$. The examples provided are conducted without recycling the unconverted reactants, with the exception of Example 6. This example, of 6 hours duration, indicates separation of the components of the reaction mixture into, on the one hand, "light components" of which 134a is one and, on the other hand, "heavy components" and 133a which are recycled to the reactor, but it gives neither the operating conditions of this separation, nor the effect of this recycling on the catalyst, not enabling the example to be reproduced.

Patent Application EP 446,869 describes a process for the preparation of 133a by fluorination in the gaseous phase of trichloroethylene conducted in the presence of inert diluents such as the gases coming from the reaction fluorinating 133a into 134a. Implementation of this integrated process for the preparation of 134a leads, as indicated in FIG. 2 of this patent application, to conducting the fluorination reaction of 133a into 134a in the presence of a recycling of unconverted reactants 133a and HF. However, the conditions for separating the products and reactants and the effects of the recycling are not indicated; the examples provided concern trials carried out in the absence of recycling, feeding with reactants being restored.

Patent Applications EP 449,614 and EP 449,617 describe processes for the preparation of 134a by fluorination of trichloroethylene in two reaction stages (fluorination of trichloroethylene, fluorination of 133a) carried out in series (fluorination of trichloroethylene, then of 133a) or in reverse series (fluorination of 133a, then of trichloroethylene). In both cases, these processes lead to conducting the fluorination reaction of 133a into 134a in the presence of a recycling of unconverted reactants 133a and HF. However, the conditions for separating the products and reactants and the effects of recycling are not indicated; in both patent applications, the examples provided concern trials carried out in the absence of recycling, feeding with reactants being restored and the duration of the trials is not indicated.

In catalytic fluorination of 133a, the degree of conversion of 133a into 134a is limited by thermodynamics. Typically, for an HF/133a mole ratio equal to 2 at the entry of the reactor and a reaction temperature of 400° C., thermodynamic equilibrium corresponds to degrees of conversion of 133a of 20% and of HF of 10%. The flow leaving the reactor therefore contains mostly unconverted reactants (133a and HF) which it is essential to recycle. For this, the main constituents of the flow leaving the reactor can be separated and then purified according to conventional techniques, in particular unconverted 133a and HF, in order to eliminate therefrom, before recycling into the reaction, problematic impurities (such as organic byproducts or water) which are generated in the reaction or brought by the raw materials and which are capable of leading to deactivation of the catalyst or of generating corrosions.

DESCRIPTION OF THE INVENTION

It has now been found that application of this conventional technique is not necessary in the case of the preparation of 134a and that, under certain conditions, an untreated mixture containing most of the unconverted 133a and HF can be recycled directly to the reactor, after separating the products HCl and 134a.

This result is particularly unexpected in the light of the existing art in which, in the absence of any recycling, that is to say with reactants of controlled purities, the reaction performances obtained (conversion, selectivity, and lifetime) are not economical.

The subject of the invention is therefore a continuous process for the preparation of 134a from 133a and HF in the gaseous phase and in the presence of a chromium-based catalyst, characterized in that the flow of gas leaving the reactor is subjected to a distillation in order to separate at the top a flow containing almost all the hydrochloric acid and at least 90% of the 134a produced by the reaction and at the bottom a flow containing at least 90% of the unconverted reactants (133a and HF) present in the flow of gas leaving the reactor, and in that the flow recovered at the bottom of the distillation is recycled directly to the reactor, without any purifying operation.

As may be expected, recycling of the unconverted reactants directly to the reactor, in the absence of special purifying of the recycled material, leads to a certain degree of accumulation of water and organic by-products in this recycled material. Curiously, in steady state, the content of water and of these organic by-products stabilizes in a stationary state and does not impair performance of the catalyst:

degree of conversion of 133a near to the state of thermodynamic equilibrium of the reaction

$$CF_3CH_2Cl + HF \rightleftharpoons CF_3CH_2F + HCl.$$

high selectivity in 134a, typically greater than 98%.

Moreover, it is observed that the water content of the recycling loop curiously stabilizes at a low value.

In implementing the process according to the invention, these performances (activity and selectivity), remain stable for at least a few hundred hours; this allows frequent operations of replacing or regenerating the catalyst, which create high investment costs and operating expenses, to be avoided. The process according to the invention is all the more cost-effective since it does not involve operations for purifying the flow to be recycled.

The chromium-based catalyst, used according to the present invention, can be a bulk catalyst or a supported catalyst.

As bulk catalysts, oxides of chromium, preferably amorphous, are mainly used as starting materials, but chromium salts such as chromium sulphate may also be used in various commercial forms. Formation of these catalysts may involve techniques which are very diverse and well known to those skilled in the art. The form of the catalyst is not critical and pellets, granules, powders or even microspheres may equally well be used. The quantity of chromium, expressed in terms of metal before processing with hydrofluoric acid, is high, generally between 20% and 68% by weight. The rest of the composition of the catalyst is generally oxygen, but may also contain other elements (for example silicon, carbon, transition metals, alkaline-earth metals, rare earths or uranium) and more generally metals belonging to groups VIII, VII B, VI B, III B, II B, and I B of the Periodic Table of the Elements.

For supported catalysts, materials such as activated carbons, alumina, aluminium trifluoride or alternatively partially fluorinated alumina may be used as supports. Partially fluorinated alumina is understood to mean a composition which is rich in fluorine and contains aluminium, oxygen and fluorine in proportions such that the quantity of fluorine expressed in terms of $AlF_3$ represents at least 50% of the total. The support may take the form of a powder or pellets.

Supported catalysts may be prepared by techniques which are well known to those skilled in the art. For example, activated carbon or partially fluorinated alumina may be impregnated with a solution containing at least one chromium salt or chromic acid $CrO_3$ and optionally a salt of another metal, for example, alkaline-earth metals, transition metals, uranium, rare earths and, more generally, metals of groups VIII, VII B, VI B, III B, IIB and I B. The chromium content of the supported catalysts is in general less than 20% by weight and contents of between 4 and 10% are in general used.

The catalyst may also be prepared by coprecipitation of the final constituents in their metal hydroxide form, then dried, and calcined in order to form mixed oxides according to techniques which are well known to those skilled in the art.

The chromium catalysts used, whether bulk or supported, are pretreated before being placed in the reaction, by HF alone or, more generally, mixed with an inert gas such as nitrogen. This treatment is in general carried out for a period of 1 to 24 hours and at a temperature of between 200° and 450° C.

The reaction itself of 133a with HF in the presence of a chromium-based catalyst according to the invention can be carried out in a temperature range of between 300° and 450° C., preferably between 330° and 400° C., with a contact time of between 0.1 seconds and 60 seconds, preferably from 5 to 30 seconds.

The pressure at which the reaction can be carried out is between atmospheric pressure and 30 bar absolute. Operation is preferably at a pressure ranging from 10 to 15 bar absolute which allows separation of anhydrous HCl from 134a to be carried out economically. Use of a high pressure furthermore enables a considerable improvement in the yield to be obtained.

The quantity of hydrofluoric acid used is at least equal to the stoichiometric value, but the HF/133a ratio for feeding the reaction is advantageously between 1 and 10, preferably 2 to 5.

For certain catalysts, it can be advantageous to work in the presence of oxygen in order to improve the lifetime of the catalyst. The quantity of oxygen used, as a proportion of the 133a feeding the reaction, may range between 0.1 and 5 mol %. Oxygen can be introduced into the reaction zone, either alone, or in a mixture with an inert gas such as nitrogen and, of course, in the form of air. The use of oxygen is not without its drawbacks in respect of the selectivity of the reaction. In fact the appearance of CO, $CO_2$ in the reaction product is noted, as is, no doubt via the Deacon reaction between HCl formed and oxygen (giving chlorine and water), the formation of by-products such as 1,1-dichloro-2,2,2-trifluoroethane (HCFC-123), 1-chloro-1,2,2,2-tetrafluoroethane (HCFC-124) and pentafluoroethane (HCFC-125). It has however been noticed that use of oxygen or air in no way interferes with downstream separation of the reaction and that the unconverted reactants (HF and 133a) and the heavy impurities which accompany them can be recycled into the reaction after separation under specified conditions without the activity of the catalyst being reduced. A stationary state allowing the loop to operate for at least a few hundred hours is reached.

The reaction of 133a with HF may be carried out in various types of reactors depending on the catalyst used, its mechanical properties and its resistance to attrition. The operation may be carried out either with a fixed bed, or with a fluidized bed and in either one or more reactors. The materials used should be resistant to corrosion by the mixture and should be, for example, Inconel or Hastelloy.

The flow of gas leaving the fluorination reactor comprises mainly HF, 133a, 134a and HCl. According to the present invention, this flow of gas is subjected to a separation by distillation so as to recover, on the one hand, almost all the HCl and at least 90% of the 134a present in this flow and, on the other hand, at least 90% of the 133a and the HF which are recycled directly into the reaction.

This separation may be carried out by distillation in one or two stages, that is to say by separating HCl then 134a or directly, and more simply, in one stage by separating HCl and 134a in a mixture. In this case most of the HCl and the 134a is obtained at the top of the distillation and most of the 134a and the HF at the bottom.

This distillation is preferably carried out in a stainless steel column which can be fitted with plates or packing. The distillation can be conducted at a pressure ranging from 1 to 30 bar absolute, depending on the pressure at which the catalytic fluorination reaction is carried out. The temperature for feeding the reaction mixture may range from 20° to 150° C. The temperature at the top depends of course on the separation yield required and varies as a function of the pressure; it is approximately 5° C. at 3 bar absolute and approximately 55° C. at 15 bar absolute.

At fixed pressure, the temperature at the top is used to regulate the content in 133a and HF of the top flow while the rate of reboiling at the bottom is used to regulate the removal of HCl and 134a. The HF passing to the top is mainly connected with azeotropes which exist with 134a and 133a.

It is observed that if most of the HCl and 90% at least of the 134a produced in the reaction are not removed, yield, but also selectivity, decrease in the reaction. In the same way, not separating and directly recycling at least 90% of the 133a and the HF present on leaving the reaction unnecessarily forces these products to be reprocessed downstream of the reaction loop.

The reaction and this distillation are preferably effected at a pressure between approximately 10 and 15 bar absolute. In fact, under these conditions, the HCl/134a mixture is itself also economically separable by distillation with the production of anhydrous hydrochloric acid. Conversely, at a pressure of the order of 2 to 3 bar absolute, the HCl/134a mixture coming from this distillation should generally be treated with water in order to remove the HCl.

The flow of unconverted reactants, obtained at the bottom of the distillation column, is not subjected to any particular treatment for purifying or removing organic or inorganic impurities. This flow, mainly composed of 133a and HF, therefore contains various organic impurities, traces of water (of the order of 1000 ppm by weight or less) and possibly a low proportion of the reaction products (134a and HCl) which have not been separated. This flow is directly recycled to the fluorination reactor. Fresh reactants (133a and HF) are furthermore fed into any point of the reaction-separation-recycling system, in proportions which allow net production of 134a and HCl to be compensated for.

Fresh reactants can be introduced either before distillation downstream from the reaction in order to cool the gases, or in the flow of unconverted reactants recycled into the reaction.

133a and HF possibly present in a low proportion in the flow of 134a and HCl coming from the top of the distillation can be further separated from the reaction products by methods which are known per se and recycled to the reactor.

EXAMPLES

The following examples illustrate the invention without thereby limiting it.

BRIEF DESCRIPTION OF THE DRAWINGS

They have been carried out in a plant shown in the single attached FIGURE. This plant comprises a reactor (2) made of Inconel with a working volume of 100 liters and a distillation column (4) made of Inox 316 L with an internal diameter of 150 mm, a height of 7800 mm and fitted with Multiknit packing made of Inox 316 L.

The fresh reactants and the flow of unconverted reactants (recycling) are fed to the reactor after preheating in an electric preheater (1). The gaseous effluent leaving the reactor is cooled in a cooling exchanger (3), then introduced into the distillation column.

Figure 1:
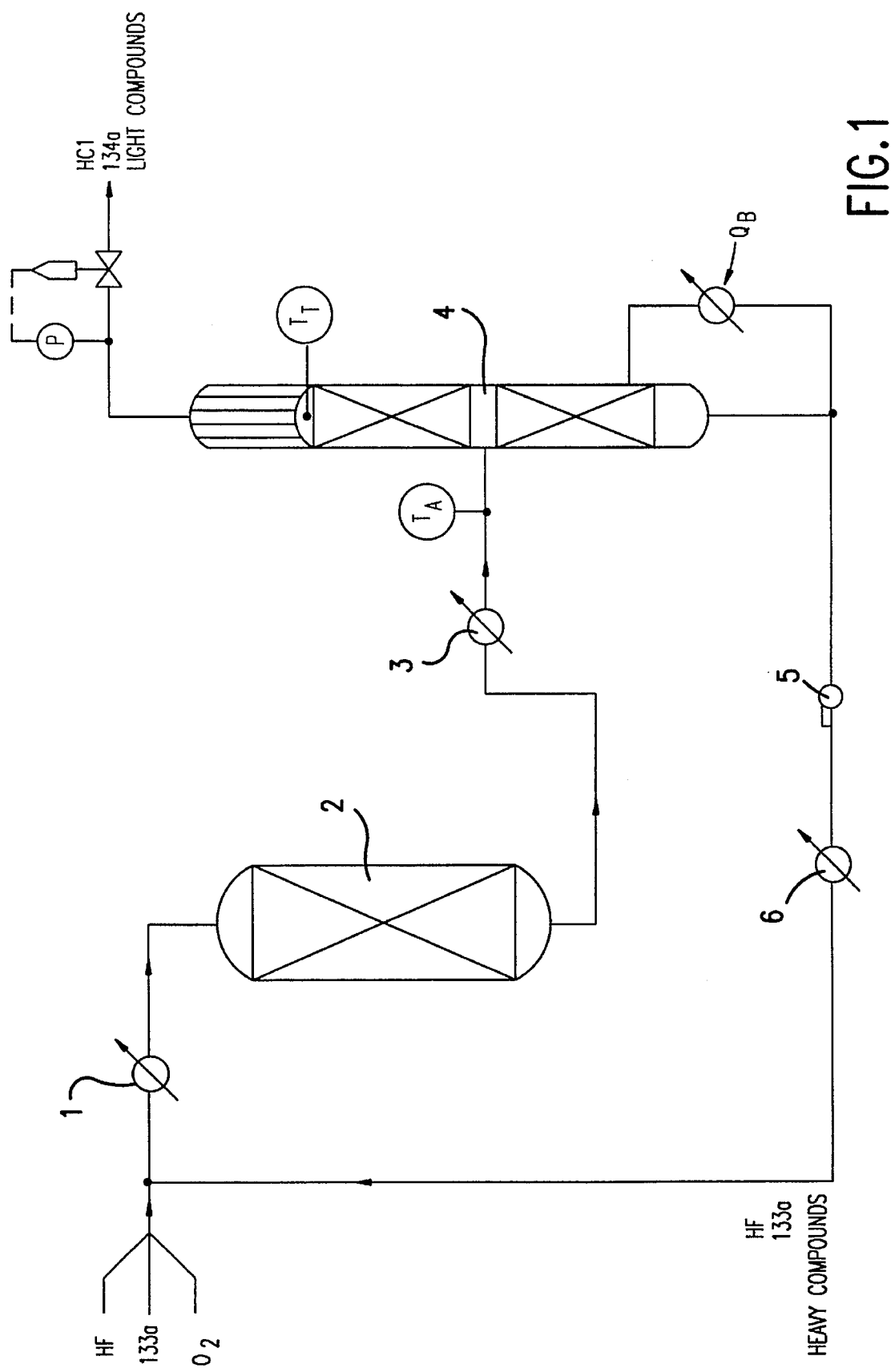

At the top of the distillation column, HCl, 134a and the light products are recovered, and at the bottom 133a, HF and the heavier products are recovered. This flow of unconverted reactants is recycled to the reactor via a pump (5) and an evaporator (6).

At the feeding point of the preheater (1), addition of fresh HF and 133a, and possibly feeding with oxygen, is carried out.

The HF used, which is technical grade, is 99.9% by weight pure and contains water as the main impurity at a level of approximately 500 to 1000 ppm.

The 133a used is 99.95% by weight pure.

EXAMPLE 1

The catalyst used is an Ni +Cr/AlF$_3$ catalyst prepared by impregnation of a partially fluorinated alumina (content by weight of AlF$_3$ greater than 78%) with chromic acid and nickel chloride hexahydrate, then reduction with methanol. Its main physico-chemical properties are as follows:

| chemical composition (by weight) | |
|---|---|
| fluorine | 46.6% |
| aluminium | 31.8% |
| nickel | 3.6% |
| chromium | 3.4% |
| oxygen | 10.2% |
| chlorine | 4.4% |
| physical properties: | |
| BET surface area | 40 m$^2$/g |
| Grain size | 1 to 2 mm beads |

This catalyst was previously treated at 350° C. for 10 hours by means of a mixture of hydrofluoric acid and nitrogen at 5 mol % HF, then at 400° C. for 5 hours by means of a mixture of hydrofluoric acid and nitrogen at 10 mol % HF.

Fluorination of 133a with this catalyst was carried out under the following operating conditions:

| a) Reaction | |
|---|---|
| reaction temperature | 350° C. |
| pressure | 3.1 bar absolute |
| contact time | 9 seconds |
| HF/133a mole ratio at the feeding point of the reactor | 4 |
| O$_2$/133a mole ratio at the feeding point of the reactor | 0.15% |
| b) Separation | |
| The distillation column intended to process the flow leaving the reactor is regulated in the following manner: | |
| feeding temperature, T$_A$ | 50° C. |
| temperature at top, T$_T$ | 5° C. |
| heat supplied to the reboiler Q$_B$ | 2.8 kW |
| pressure | 3.1 bar absolute |

These operating conditions enabled a flow of 134a and HCl to be obtained at the top and a flow of 133a and HF to be obtained at the bottom such that:

the contents in 134a and HCl of the flow of recycled 133a and HF were less than 100 ppm, which corresponds to degrees of recovery of more than 99.7% for these two products the molar contents in 133a and HF in the flow of 134a and HCl were respectively 2.3% and 14.4%, which corresponds to degrees of recovery of 98.7% for 133a and 98.3% for HF.

After 700 hours of operation, the performances observed are as follows:

a) Conversion of 133a per pass=19.5%. The term conversion is understood to mean the ratio between the 133a consumed and the 133a entering the reactor.

b) Selectivity in 134a per pass=98.8%. The term selectivity in 134a is understood to mean the ratio between the 134a produced and the consumed 133a.

The following main impurities are observed in the flow of reaction products recovered at the top of the distillation column: CF$_3$—CHClF (124), CHCl=CF$_2$(1122), CF$_3$—CHF$_2$(125), CF$_3$—CH$_3$(143a), CClF$_3$(13), CHF$_3$ (23), O$_2$, CO and CO$_2$.

c) Yield of 134a=97 g/h/litre of catalyst.

d) Water content of the recycled flow: several analyses of the recycled flow were carried out throughout this trial in order to determine its water content (Karl Fischer method). The results showed that there was no build up of water and that the H$_2$O content in the recycled flux was between 600 and 800 ppm by weight.

e) Content of inorganic impurities in the recycled material: several analyses of the recycled flow were carried out throughout this trial in order to determine the content of organic impurities in this flow. The results showed that there was no build up and that the content of impurities was steady. This content, expressed in ppm in moles in relation to the total recycled flow, is less than 300 ppm. The main impurities are: CHCl$_2$—CF$_3$ (123) and CHClF-CF$_3$ (124).

EXAMPLE 2

The catalyst used in this example is a bulk chromium catalyst whose main physico-chemical properties are the following:

| Chemical composition (by weight) | |
|---|---|
| chromium | 68% |
| oxygen | 32% |
| Physical properties: | |
| Grain size (mean diameter) | 0.5 mm |
| BET surface area | 50 m$^2$/g |

This catalyst, previously treated by means of an HF and N$_2$ mixture (30 mol %) at 350° C. for 5 hours, was used in the absence of oxygen under the following operating conditions:

| a) Reaction: | |
|---|---|
| reaction temperature | 350° C. |
| pressure | 3 bar absolute |
| contact time | 7 seconds |
| HF/133a mole ratio at the feeding point of the reactor | 4 |
| b) Separation: | |
| The distillation column was regulated in the following manner: | |
| feeding temperature, T$_A$ | 50° C. |
| temperature at top, T$_T$ | 3° C. |
| heat supplied to the reboiler, Q$_B$ | 4.7 kW |

| | |
|---|---|
| pressure | 3 bar absolute |

Under these conditions, the contents of 134a and HCl of the recycled 133a and HF flow were less than 100 ppm which corresponds to degrees of recovery of 134a and HCl of more than 99.5%.

Moreover, the molar contents of 133a and HF in the 134a and HCl flow recovered at the top of the distillation column were respectively 1.4% and 10.7%, which corresponds to degrees of recovery of 99.2% for 133a and 98.7% for HF.

After 260 hours of operation, the performances observed are as follows:

a) Conversion of 133a per pass : 15% b) Selectivity in 134a per pass : 99.5%

The following main impurities are observed in the flow of reaction products recovered at the top of the distillation column: $CF_3$—CHClF (124), $CHCl=CF_2$ (1122), $CF_3$—$CHF_2$ (125), $CF_3$—$CH_3$ (143a), $CClF_3$ (13) and $CHF_3$ (23).

c) Yield of 134=92 g/h/liter of catalyst d) Water content in the recycled flow: several analyses of the recycled flow were carried out throughout this trial in order to determine its water content. The results showed that there was no build up of water and that the content of $H_2O$ in the recycled flow was between 500 and 700 ppm by weight.

e) Content of organic impurities in the recycled material: several analyses of the recycled flow were carried out throughout this trial in order to determine the content of organic impurities in this flow. The results showed that there was no build up and that the content of impurities was steady. This content, expressed in ppm in moles in relation to the total recycled flow, is less than 400 ppm. The main impurity is $CHCl_2CF_3$ (123). EXAMPLE 3

The catalyst used is an Ni+Cr/AlF$_3$ catalyst, prepared in the same way as in Example 1, but with higher contents of chromium and nickel. Its main physico-chemical properties are the following:

| Chemical composition (by weight) | |
|---|---|
| fluorine | 41.5% |
| aluminium | 28.3% |
| nickel | 6.4% |
| chromium | 5.9% |
| oxygen | 10.3% |
| chlorine | 7.6% |
| Physical properties: | |
| BET surface area | 50 m$^2$/g |
| Grain size | 1 to 2 mm beads |

This catalyst was previously processed by means of a hydrofluoric acid and nitrogen mixture with 5 mol% HF between 260° C. and 300° C. for 10 hours, then with 10 mol % HF at 350° C. for 4 hours.

Fluorination of 133a is carried out under the following operating conditions:

| | |
|---|---|
| a) Reaction: | |
| reaction temperature | 350° C. |
| pressure | 12 bar absolute |
| contact time | 24 seconds |
| HF/133a mole ratio at the feeding point of the reactor | 2 |
| O$_2$/133a mole ratio at the feeding point of the reactor | 0.7% |
| b) Separation: | |
| The distillation column was regulated in the following manner: | |
| feeding temperature, T$_A$ | 100° C. |
| temperature at top, T$_T$ | 63° C. |
| heat supplied to the reboiler, Q$_B$ | 12.5 kW |
| pressure | 12 bar absolute |

These operating conditions enabled a flow of 134a and HCl to be obtained at the top and a flow of 133a and HF to be obtained at the bottom such that:

in the recycled flow the molar contents of HCl and 134a were respectively 0.1% and 0.5%, which corresponds to degrees of recovery of approximately 98.2% for HCl and 91% for 134a;

the molar contents of 133a and HF in the flow recovered at the top of the distillation column were respectively 3.0% and 13%, which corresponds to degrees of recovery of 98.8% for 133a and 97.7% for HF.

After 600 hours of operation, the performances observed are as follows:

a) Conversion of 133a per pass : 15% b) Selectivity in 134a per pass : 98.8%

The impurities observed in the flow of reaction products recovered at the top of the distillation column are identical to those cited in Example 1.

c) Yield in 134a=180 g/h/litre of catalyst d) Water content in the recycled flow: the analyses carried out throughout this trial showed that there was no build up of water in the recycled flow. The water content in this flow is between 600 and 800 ppm by weight.

e) Content of organic impurities in the recycled material: the analyses carried out throughout this trial showed that there was no build up of organic impurities in the flow recycled to the reaction. The content of organic impurities is steady and less than 500 ppm in moles. The main impurities are identical to those cited in Example 1.

We claim:

1. Continuous process for the preparation of 1,1,1 2-tetrafluoroethane (134a) from 2-chloro-1,1,1-trifluoroethane (133a) and hydrofluoric acid in the gaseous phase in the presence of a chromium-based catalyst, comprising subjecting the flow of gas leaving the reactor to a distillation in order to separate at the top a flow containing almost all the hydrochloric acid and at least 90% of the 134a produced by the reaction and at the bottom a flow containing at least 90% of the unconverted reactants (133a and HF) present in the flow of gas leaving the reactor, and the flow recovered at the bottom of the distillation, including water and organic by-products, is recycled directly to the reactor, without any purifying operation.

2. Process according to claim 1, whichin the reaction and the distillation are conducted at a pressure ranging from 1 to 30 bar absolute, preferably at a pressure of between approximately 10 and 15 bar absolute.

3. Process according to claim 1 wherein the chromium-based catalyst is a bulk catalyst or a supported catalyst.

4. Process according to claim 1, wherein the fluorination reaction is carried out at a temperature of between 300° and 450° C.

5. Process according to claim 1, wherein the contact time is between 0.1 and 60 seconds.

6. Process according to claim 1, wherein the HF/133a mole ratio entering the reaction is between 1 and 10.

7. Process according to claim 1, wherein the reaction is carried out in the presence of oxygen in the ratio of 0.1 to 5 mol oxygen to 100 mol of 133a entering the reaction.

8. Process according to claim 4, wherein the reaction temperature is between 330° and 400° C.

9. Process according to claim 5, wherein the contact time is between 5 and 30 seconds.

10. Process according to claim 6, wherein the mole ratio is between 2 and 5.

11. A continuous process for the preparation of 1,1,1 2-tetrafluoroethane (134a) comprising the steps of:
   (a) flowing a fresh gaseous reactants stream comprising 2-choro-1,1,1 2-trifluoroethane (133a) and hydrofluoric acid, and a recycled gaseous unconverted reactants stream comprising 2-chloro-1,1,1-trifluoroethane (133a) and hydrofluoric acid into a reactor having a chromium based catalyst therein, wherein said reactor communicates with a vertically oriented distillation column having a top, bottom and middle;
   (b) contacting said fresh reactants and recycled unconverted reactants streams in said reactor with said catalyst, whereby a reaction occurs and a gaseous effluent is provided comprising reaction products and the unconverted reactants, wherein said reaction products comprise 1,1,1,2 tetrafluoroethane and hydrochloric acid;
   (c) flowing said gaseous effluent directly into the middle of said column;
   (d) separating the reaction products from the unconverted reactants in the column by flowing light products to the top of said column and flowing heavy products to the bottom of said column;
   (e) collecting the reaction products from the top of said column;
   (f) flowing unconverted reactants, water and organic by-products from the bottom of said column directly to the reactor without any purification operation to provide the recycled unconverted reactants stream.

12. The process of claim 11 further comprising the step of cooling the gaseous effluent once it has left the reactor and prior to its introduction into the distillation column.

13. The process of claim 11 further comprising the step of preheating the fresh reactants prior to flowing them into the reactor.

14. The process of claim 13 further comprising the step of regulating the distillation column by maintaining a feed temperature of about 50° C. to 100° C., a temperature at the top of about 3° C. to 63° C., and a pressure which is the same as that in the reactor.

15. The process of claim 14 further comprising the step of heating the recycled unconverted reactants prior to introduction into the reactor.

16. The process of claim 15 wherein the step of contacting is carried out at about 350° C.

17. The process of claim 11 wherein the reactor and the column are at a pressure ranging from 1 to 30 bar absolute; and wherein the reaction in the reactor is carried out at a temperature of between 300° and 450° C., a contact time between 0.1 and 60 seconds, a HF/133a mole ratio entering the reaction of between 1 and 10, and in the presence of oxygen in the ratio of 0.1 to 5 mol oxygen to 100 mol of 133a entering the reactor.

18. The process of claim 11 wherein the reaction product collected at the top of said column contain almost all the hydrochloric acid and at least 90% of the 134a produced by the reaction, and wherein the unconverted reactants stream flowing from the bottom of said column contains at least 90% of the unconverted 133a and hydrofluoric acid present in the flow of gas leaving the reactor.

19. The process of claim 11 wherein the amount of water and organic by-products from the bottom of said column stabilizes in the recycled unconverted reactants stream without impairing performance of the catalyst.

20. Continuous process for the preparation of 1,1,1,2-tetrafluoroethane (134a) from 2-chloro-1,1,1-trifluoroethane (133a) and hydrofluoric acid in the gaseous phase in the presence of a chromium-based catalyst, comprising subjecting the flow of gas leaving the reactor to distillation in a distillation column in order to separate at the top of the column a stream containing almost all the hydrochloric acid and at least 90% of the 134a produced by the reaction and at the bottom of the column a stream containing at least 90% of the unconverted reactants (133a and HF) present in the flow of gas leaving the reactor, and the stream recovered at the bottom of the column, including water and organic by-products, is recycled directly to the reactor without any purifying operation, the amount of water and organic by-products in the recycled stream stabilizing without impairing performance of the catalyst.

* * * * *